US011185345B2

(12) United States Patent
Edwards (10) Patent No.: US 11,185,345 B2
(45) Date of Patent: Nov. 30, 2021

(54) DEBRIDER WITH EXTERNAL IRRIGATION SUPPLY CHANNEL

(71) Applicant: GYRUS ACMI, INC., Southborough, MA (US)

(72) Inventor: Kevin C. Edwards, Olive Branch, MS (US)

(73) Assignee: Gyrus Acmi, Inc., Westborough, MA (US)

( * ) Notice: Subject to any disclaimer, the term of this patent is extended or adjusted under 35 U.S.C. 154(b) by 111 days.

(21) Appl. No.: 15/884,488

(22) Filed: Jan. 31, 2018

(65) Prior Publication Data

US 2019/0231379 A1     Aug. 1, 2019

(51) Int. Cl.
| | | |
|---|---|---|
| *A61B 17/3205* | (2006.01) | |
| *A61M 3/02* | (2006.01) | |
| *A61B 17/32* | (2006.01) | |

(52) U.S. Cl.
CPC .... *A61B 17/3205* (2013.01); *A61B 17/32002* (2013.01); *A61M 3/0283* (2013.01); *A61B 2017/320004* (2013.01); *A61B 2217/005* (2013.01); *A61B 2217/007* (2013.01)

(58) Field of Classification Search
CPC .............. A61B 17/32; A61B 17/32002; A61B 17/3203; A61B 17/3205; A61B 2017/320004; A61B 2217/005; A61B 2217/007; A61B 17/3207; A61B 17/320708; A61B 17/320725; A61B 17/320758; A61B 17/320783; A61B 17/3209; A61B 2017/320024; A61B 2017/320028; A61B 2017/320032; A61B 2017/320716; A61B 2017/320733; A61B 2017/320741; A61B 2017/320766; A61B 2017/320775; A61M 3/0283
USPC ......................................................... 606/167
See application file for complete search history.

(56) References Cited

U.S. PATENT DOCUMENTS

| | | | | |
|---|---|---|---|---|
| 5,782,795 | A | | 7/1998 | Bays et al. |
| 6,007,556 | A | * | 12/1999 | Kablik ............. A61B 17/32002 606/180 |
| 6,042,593 | A | * | 3/2000 | Storz ................ A61B 17/32002 606/159 |

(Continued)

FOREIGN PATENT DOCUMENTS

| | | |
|---|---|---|
| CN | 1665450 | 9/2005 |
| CN | 102006829 | 4/2011 |

(Continued)

OTHER PUBLICATIONS

European Extended Search Report for European Application 19150618.7; dated Jul. 17, 2019.

(Continued)

*Primary Examiner* — Diane D Yabut
*Assistant Examiner* — Christina C Lauer
(74) *Attorney, Agent, or Firm* — Schwegman Lundberg & Woessner, P.A.

(57) ABSTRACT

A debrider that includes an outer member, an inner member located inside of the outer member, and an irrigation supply channel configured to supply irrigation fluid to a distal portion of an aspiration channel defined inside the inner member. The irrigation supply channel is located outside of the outer member.

10 Claims, 3 Drawing Sheets

(56) References Cited

U.S. PATENT DOCUMENTS

| | | | |
|---|---|---|---|
| 6,183,433 B1* | 2/2001 | Bays | A61B 17/32002 |
| | | | 604/22 |
| 6,214,009 B1* | 4/2001 | Toriumi | A61B 17/32002 |
| | | | 606/80 |
| 6,293,957 B1 | 12/2001 | Peters et al. | |
| 6,423,078 B1* | 7/2002 | Bays | A61B 17/32 |
| | | | 606/131 |
| 6,610,059 B1 | 8/2003 | West, Jr. | |
| 7,226,459 B2 | 6/2007 | Cesarini et al. | |
| 7,510,563 B2 | 3/2009 | Cesarini et al. | |
| 7,666,200 B2 | 2/2010 | Heisler | |
| 9,226,792 B2* | 1/2016 | Bloom | A61B 18/1445 |
| 2003/0060862 A1 | 3/2003 | Goble et al. | |
| 2003/0097129 A1* | 5/2003 | Davison | A61B 18/14 |
| | | | 606/41 |
| 2005/0054972 A1* | 3/2005 | Adams | A61B 17/32002 |
| | | | 604/22 |
| 2015/0018711 A1* | 1/2015 | Furlong | A61B 1/00094 |
| | | | 600/565 |
| 2015/0282833 A1 | 10/2015 | Yoon et al. | |
| 2016/0235474 A1 | 8/2016 | Prisco et al. | |
| 2016/0345997 A1* | 12/2016 | Nguyen | A61B 17/3205 |
| 2018/0070981 A1* | 3/2018 | Govari | A61B 17/24 |
| 2019/0231378 A1* | 8/2019 | Church | A61B 17/24 |

FOREIGN PATENT DOCUMENTS

| | | | |
|---|---|---|---|
| CN | 102458275 | 5/2012 | |
| CN | 103327911 | 9/2013 | |
| CN | 104203128 | 12/2014 | |
| CN | 104220016 | 12/2014 | |
| EP | 3345557 A1 * | 7/2018 | ....... A61B 17/32002 |
| EP | 3524186 B1 | 6/2021 | |
| JP | H05220157 A | 8/1993 | |
| WO | 2014106847 | 7/2014 | |

OTHER PUBLICATIONS

"European Application Serial No. 19150618.7, Response filed Feb. 13, 2020 to Extended European Search Report dated Jul. 17, 2019", 9 pgs.

"Japanese Application Serial No. 2019-012976, Notification of Reasons for Rejection dated Dec. 3, 2019", w/ English Translation, 12 pgs.

"Japanese Application Serial No. 2019-012976, Response filed Apr. 22, 2020 to Notification of Reasons for Rejection dated Dec. 3, 2019", w/ English Claims, 11 pgs.

"Japanese Application Serial No. 2019-012976, Notification of Reasons for Refusal dated Oct. 6, 2020", w/o English Translation, 4 pgs.

"Chinese Application Serial No. 201910072653.3, Office Action dated Dec. 30, 2020", with English translation of claims, 21 pgs.

"Chinese Application Serial No. 201910072653.3, Response filed May 13, 2021 to Office Action dated Dec. 30, 2020", w/ English Claims, 15 pgs.

"Japanese Application Serial No. 2019-012976, Response filed Mar. 15, 2021 to Notification of Reasons for Refusal dated Oct. 6, 2020", w/English Claims, 10 pgs.

"Chinese Application Serial No. 201910072653.3, Office Action dated Aug. 23, 2021", w English Translation, 13 pgs.

* cited by examiner

DEBRIDER WITH EXTERNAL IRRIGATION SUPPLY CHANNEL

FIELD

These teachings relate to a medical device, and more particularly to a debrider with an external irrigation supply channel.

BACKGROUND

A debrider is a medical device that includes an inner member located within an outer member. The inner member is configured to rotate and/or reciprocate within the outer member. The inner member comprises a cutting portion, and the outer member comprises a cutting window that is configured to expose the cutting portion of the inner member. During a medical procedure, the cutting portion may be used to shave, cut, resect, abrade, or otherwise remove portions of tissue, bone, or other anatomical features or objects at a surgical site. The shaved, cut, resected, abraded, or removed portions of the tissue, bone, or other anatomical features may be directed into an aspiration channel defined inside the inner member, and then removed from the aspiration channel and surgical site by passing irrigation fluid through aspiration channel and/or drawing suction or vacuum inside the aspiration channel.

Typically, the irrigation fluid is introduced into the debrider at a proximal location of the debrider, into a gap defined between the inner and outer members, and moved distally until the irrigation fluid enters the inner member window and then the aspiration channel. However, the gap defined between the inner and outer members is typically relatively small, particularly at a distal end of the debrider where a distal bearing may be located between the two members, for example. The small space between the two members may limit or reduce the amount of irrigation fluid that enters the aspiration channel, which may thus limit the effectiveness of the irrigation fluid in moving the matter, which may ultimately lead to a build-up or accumulation of matter inside the aspiration channel resulting in a clogged aspiration channel. A clogged aspiration channel may interfere with or inhibit the cutting portion of the debrider from properly or effectively shaving, cutting, resecting, abrading, or removing additional portions of the tissue, bone, or other anatomical features. A clogged aspiration channel may inhibit or prevent removal of additional shaved, cut, resected, abraded, or removed portions of the tissue, bone, or the other anatomical features from the surgical site, which may contaminate the surgical site and/or make it difficult for the clinician performing the medical procedure to see the surgical site.

It may therefore be desirable to improve the current state of the art by providing a debrider with an improved irrigation supply to reduce or minimize changes of matter building up or clogging inside the aspiration channel. Some examples of debriders are disclosed in U.S. Pat. Nos. 6,007,556, 6,293,957, 7,226,459, 7,510,563, and 7,666,200.

SUMMARY

These teachings provide a debrider. The debrider comprises an inner member that is located within an outer member. The debrider comprises an irrigation supply channel that is located outside of the outer member. The irrigation supply channel is configured to supply irrigation fluid to the debrider, and more particularly to the aspiration channel inside the inner member. In some configurations, the irrigation supply channel is configured to supply the irrigation fluid to a distal end of the debrider. In some configurations, the irrigation supply channel is configured to supply the irrigation fluid to a location that is distal of an outer member window, an inner member window, or both, yet proximal of a distal-most end of the debrider. In some configurations, the irrigation supply channel is configured to supply the irrigation fluid to a distal-most end of the debrider.

These teachings provide a method of using a debrider, including steps of inserting the debrider according to any of the teachings herein into a surgical site, and cutting tissue at the surgical site with the debrider.

These teachings provide a debrider that includes an outer member, an inner member located inside of the outer member, the inner member comprising an aspiration channel; and an irrigation supply channel configured to supply irrigation fluid to a distal portion of the aspiration channel. The irrigation supply channel is located outside of the outer member, and is fluidly connected to a distal portion of the outer member.

These teachings provide a method that includes: an outer member comprising an outer member irrigation opening; an inner member located inside of the outer member. The inner member comprising an aspiration channel, a cutting portion, and an inner member irrigation opening. An irrigation supply channel is in fluid communication with both of the outer member irrigation opening and the inner member irrigation opening and is configured to supply irrigation fluid to a distal portion of the aspiration channel by supplying the irrigation fluid through both of the outer member irrigation opening and the inner member irrigation opening. The irrigation supply channel is located outside of the outer member. Both of the outer member irrigation opening and the inner member irrigation opening are located distal of the cutting portion of the inner member.

These teachings provide a system a system comprising the debrider according to an of the teachings herein. The system comprises a fluid source that is in fluid communication with the irrigation supply channel and is configured to provide the irrigation fluid to the debrider. The system comprises a suction source that is in fluid communication with the aspiration channel and is configured to draw the irrigation fluid in a proximal direction through the aspiration channel.

DETAILED DESCRIPTION

These teachings provide a medical device. The medical device may be a shaver, a debrider, or a microdebrider. The medical device may function to shave, cut, resect, abrade, or otherwise remove portions of tissue, bone, or other anatomical features and/or objects at or from a surgical site, such as a body cavity. For example, the medical device may be used in joint surgery, plastic surgery, various otolaryngologic procedures, including, but not limited to, sinus surgery and tonsillectomy, or a combination thereof.

The medical system may comprise one or more energy sources. The energy source may function to power the medical device, power the suction source, power the irrigation source, or a combination thereof. The energy source may function to cause the inner member to reciprocate, rotate, and/or oscillate. For example, the energy source may function to cause the inner tubular member to rotate relative to the outer member, the hand piece, or both in a clockwise direction, a counter clockwise direction, or both. The energy source may function to cause the inner member to move or reciprocate between a proximal position and a distal position relative to the outer member, the hand piece, or both. The energy source may function to cause the suction source to generate suction or draw vacuum to move, draw, or suck matter, fluids, liquids, irrigation fluid, or a combination thereof located inside the aspiration channel in a proximal direction. The energy source may function to cause the irrigation source to supply irrigation fluid to the medical device, pull or draw irrigation away from the medical device, or a combination thereof.

The energy source may be an AC energy source, a DC energy source, or both. The energy source may be a single energy source that powers the entire medical system. The energy source may be one or more energy sources that power the medical device, the irrigation source, the suction source. The energy source may be located away from the medical device, the suction source, the irrigation source, and may be connected thereto, or therewith, with one or more electrical conductors or cords. Additionally, or alternatively, the energy source may be contained within, or may be part of, the medical device. For example, the energy source may be contained within the hand piece. Additionally, or alternatively, the energy source may be contained within, or may be part of the suction source. Additionally, or alternatively, the energy source may be contained within, or may be part of the irrigation source.

The medical system may comprise one or more suction sources. The suction source may function to pull, suck, draw, aspirate or otherwise move or remove shaved, cut, resected, abraded, or removed tissue, bone, or the other anatomical features, objects, and/or fluid, also referred to herein collectively as "matter", from within the outer member, the inner member, the aspiration channel, the medical device, the cutting window, the cutting portion, or a combination thereof. The matter may be moved into a receptacle that is located at a proximal end of the medical device, inside the hand piece, or at a location away from the medical device, for example into the suction source. The suction source may perform the aforementioned functions by generating and applying vacuum, suction, negative pressure to the medical device, the aspiration channel, or both. The suction source may be fluidly connected to the medical device and the one or more aspiration channels via one or more tubes or hoses.

The suction source may be part of the medical device. For example, the suction source may be contained within the hand piece. The suction source may be a discrete component that is separate from the medical device, and connected thereto via one or more tubes or wires. The suction source may be powered by the energy source that powers the medical device, or may be powered by its own discrete energy source.

The suction source may be turned ON and OFF by manipulating one or more of the user controls. The suction source may turn ON automatically when the medical device is powered (i.e., when the inner member is rotating and/or reciprocating and/or when the irrigation source is supplying irrigation fluid to the medical device), and the suction source may be turned OFF automatically when the medical device is not powered (i.e., when the inner member is not rotating and/or reciprocating and/or when the irrigation source ceases to supply or is not supplying irrigation fluid to the medical device). The suction source may be independently turned ON and OFF while the inner member is or is not rotating and/or reciprocating and/or when the irrigation source is or is not supplying irrigation fluid to the medical device.

The medical system may comprise an irrigation source. The irrigation fluid may function to assist in the removal of matter from within the aspiration channel. The irrigation fluid may function to provide cooling and/or transfer heat from the inner member and/or the outer member, which may be generated when the inner member is rotated and/or reciprocated within the outer member.

The irrigation fluid may be gravity fed or pressurized to, through, and away from the tubular assembly, the medical device, the irrigation supply channel, the aspiration channel, or a combination thereof. More specifically, the irrigation fluid is supplied by the irrigation source to the medical device by passing the irrigation fluid through the one or more external fluid supply channels in a distal direction. The irrigation fluid may then be drawn or aspirated into the aspiration channel via gravity and/or the suction source, and then moved in a proximal direction inside the aspiration channel by the suction source. The flow of irrigation fluid in a proximal direction inside the aspiration channel may function to move matter located inside the aspiration channel in a proximal direction. The flow of irrigation fluid in a distal direction inside the external irrigation supply channel and/or in a proximal direction inside the aspiration channel may function to reduce or remove heat from the inner member and/or the outer member, which may be generated when the inner member is rotated and/or reciprocated within the outer member.

In some configurations, in addition to supplying the irrigation fluid to the medical device or tubular assembly via the one or more external irrigation supply channels, irrigation fluid may also be supplied to the medical device or tubular assembly via a gap defined between the inner and outer members. This irrigation fluid may flow inside this gap in a distal direction until the irrigation fluid is directed into the aspiration channel defined inside the inner member where the irrigation fluid mixed with other irrigation fluid that was supplied into the aspiration channel via the eternal irrigation supply channel. By having two paths supplying irrigation fluid to the medical device, additional volume of irrigation fluid can be provided to the medical device.

The irrigation fluid may be provided to the medical device via the external supply channel and the gap defined between the inner and outer members simultaneously or selectively. That is, the medical device may be configured to always deliver irrigation fluid through both the external supply channel and the gap between the inner and outer members. Alternatively, the medical device may be configured to always deliver irrigation fluid through only one of the external supply channel and the gap between the inner and outer members, and only deliver the irrigation fluid through the other pathway by manipulating one of the user controls, discussed below. This may advantageously allow a clinician to regulate how much irrigation fluid is used during a medical procedure, for example, by providing additional fluid when more tissue is cut of shaved and/or when a clog develops inside the aspiration channel.

The irrigation source may comprise one or more pumps that are configured to move the irrigation fluid from the irrigation source and/or a location where the irrigation fluid is contained, to and through the external fluid supply channels, the gap defined between the inner and outer members, and then to and through the aspiration channel. The irrigation source may also comprise a bag that is elevated relative to the medical device and/or surgical site, and gravity is used to supply the irrigation source from the bag to the external fluid supply channels and to and through the aspiration channel.

The medical device comprises a hand piece. The hand piece may function to be held by a user. The hand piece may comprise a motor that may be configured to cause the inner member to rotate and/or reciprocate within and/or relative to the outer member, hand piece or both.

The hand piece may contain the energy source for operating the medical device, the medical system, or both. The hand piece may contain the suction source. The hand piece may contain a container or reservoir for collecting the matter that is pulled, sucked, drawn, aspirated or otherwise moved out of or away from the aspiration channel, the cutting portion or window, or surgical site via the suction source.

The medical system, the medical device, the hand piece, or a combination thereof may comprise one or more user controls. The one or more user controls may function to operate the medical system and/or the medical device. Manipulation of the one or more user controls may function to start and stop the medical device, the suction source, the irrigation source, or a combination thereof.

For example, manipulation of the one or more user controls may function to change (i.e., increase or decrease) a rotational speed and/or reciprocating speed of the inner member. Manipulation of the one or more user controls may function to change a rotational direction (clockwise or counterclockwise) of the inner member. Manipulation of the medical device may function to rotate the outer member clockwise or counterclockwise relative to the inner member, the hand piece, the site of interest, or a combination thereof.

For example, manipulation of the one or more user controls may function to start and/or stop the irrigation source, and/or increase or decrease the amount and/or flow rate of irrigation fluid provided to the medical device.

For example, manipulation of the one or more user controls may function to provide flow of the irrigation fluid to the external irrigation supply channel and the gap between the inner and outer members. For example, manipulation of the one or more user controls may function to provide flow of the irrigation fluid to only one of the external irrigation supply channel and the gap between the inner and outer members. For example, manipulation of the one or more user controls may function to cease flow of the irrigation fluid to one or both of the external irrigation supply channel and the gap between the inner and outer members.

For example, manipulation of the one or more user controls may function to start and/or stop the suction source, and/or increase or decrease the amount of suction or vacuum provided by the suction source to the medical device.

The one or more user controls may include one or more triggers, wheels, levers, buttons, knobs, the like, or a combination thereof. A user control may also include a foot pedal. The user controls may be located on the hand piece, on the tubular assembly, on the suction source, on the irrigation source, on the energy source, at a remote location (i.e., a foot pedal, for example), or a combination thereof.

The medical device, the tubular assembly, or both comprises one or more outer members. The outer member may function to house, contain, and protect the inner member, the cutting portion of the inner member, or both.

The outer member may be an elongated member that extends along a longitudinal axis. A proximal end of the outer member may be connected to the hand piece. A distal end of the outer member may comprise one or more cutting windows. The outer member may be the portion of the medical device that is inserted into a body cavity, anatomy, or surgical site during a medical procedure.

The outer member may be at least partially hollow, and may define therein an inner portion or channel. The hollow or inner portion of the outer member may be sufficiently sized so that one or more inner members can be received therein and/or moved therein.

The outer member may be stationary. Stationary means that the outer member does not move, rotate, and/or reciprocate, relative to the hand piece, the inner member, the site of interest, or a combination thereof. However, in some configurations, the outer member may be rotated about its center or longitudinal axis relative to the inner member, the hand piece, the site of interest, or a combination thereof. Rotating the outer member allows a rotational position of the outer window to change to be adjusted, thus exposing the cutting portion of the inner member at various rotational positions. This may allow a clinician to cut, shave, resect, debride and/or remove portions of an object or anatomical feature at various locations, without requiring the clinician to reorient the medical device and/or change their handling or approach with the medical device relative to the object or anatomical feature.

The outer member may be substantially straight or may include substantially straight or linear portions; may include one or more angles, bends or arcs; or a combination thereof. The outer member may be entirely substantially rigid, substantially flexible, or substantially resilient. The outer member may include portions that are substantially rigid, substantially flexible, substantially resilient, or a combination thereof.

The outer member may comprise one or more outer member windows. The outer member window may function to provide access to the inner member, the cutting portion of the inner member, the inner member window of the inner member, the aspiration channel, or a combination thereof.

When the inner member window or the cutting portion of the inner member is axially and/or rotationally aligned with outer member window of the outer member, objects and/or anatomical features can be shaved, cut, resected, and/or abraded. When the inner member window and/or the cutting portion of the inner member is not axial and/or rotationally aligned with outer member window of the outer member, objects and/or anatomical features are not shaved, cut, resected, and/or abraded.

The outer member window may be located anywhere along a length of the outer member. Preferably, however, the outer member window is aligned with or located proximal of any of the inner and/or outer member irrigation openings. However, in some configurations, it may be desirable to have the outer member window located distal of the inner and/or outer member irrigation openings.

The outer member window may be generally aligned with the inner member window, or may be offset from the inner member window.

The outer member window may be a notch, groove, cutout, opening, or absence of material defined or existing in a portion of the circumference of an outer surface of the outer member. The outer member window may have edges at the perimeter of the outer member window defining the outer member window, which may be sharp or serrated to assist in shaving, cutting, resecting, abrading, or otherwise removing tissue, bone, or other anatomical features or objects at the surgical site.

The outer member may comprise one or more outer member irrigation openings. The outer member irrigation opening may function to provide a passageway, path, or opening into the outer member so that irrigation fluid can be provided into the tubular assembly, into the inner member irrigation opening, into the aspiration channel, or a combination thereof. The outer member irrigation opening may function to provide an area or structure for connecting the distal irrigation port of the irrigation supply channel to the tubular assembly and/or the medical device.

The outer member irrigation opening may be a notch, groove, cutout, opening, or absence of material defined or existing in a portion of the circumference of an outer surface of the outer member. The outer member window may comprise a port, a socket, a fitting, or other structure for attaching to the irrigation supply channel without having any of the irrigation fluid leak or spill therebetween.

The outer member irrigation opening may be located anywhere on the outer member. For example, the outer member opening may be located at a distal-most end of the tubular assembly and/or outer member. The outer member irrigation opening may be located proximal of the distal-most end of the tubular assembly and/or outer member. The outer member irrigation opening may be generally aligned with or located immediately adjacent the inner member irrigation opening so that the irrigation fluid can pass through or between the inner and outer member irrigation openings without changing flow directions. The outer member irrigation opening may be offset from the inner member irrigation opening so that the irrigation fluid changes flow directions when can passing through or between the inner and outer member irrigation openings.

In configurations where the medical device comprises more than one irrigation supply channel, the outer member may comprise a corresponding number of outer member irrigation openings. In such configurations, the outer member irrigation openings may be located on the same side of the outer member, the outer member irrigation openings may be located on different sides of the outer member, and may directly oppose one another, or they may be offset from each other.

In configurations having more than one irrigation supply channel, the outer member may still only include a single outer member irrigation opening, which is configured to receive irrigation fluid from multiple supply channels.

The medical device, the tubular assembly, or both comprise one or more inner members. The inner member may be supported, provided, or contained inside the outer member. The inner member may be concentric with the outer member, or may be offset to a side of the outer member.

The inner member may be at least partially hollow and may define therein one or more aspiration channels. The inner member may be substantially straight or include substantially straight or linear portions; may include one or more angles, bends or arcs; or a combination thereof. The inner member may be entirety substantially rigid, substantially flexible, or substantially resilient. The inner member may include portions that are substantially rigid, substantially flexible, substantially resilient, or a combination thereof.

The inner member may be rotated within the outer member. The inner member may be rotated in a clockwise direction, a counterclockwise direction, or both. The inner member may be oscillated within the outer member. The inner member may be rotated or oscillated about or around its center longitudinal axis, which may, or may not be, the same as the center or longitudinal axis of the aspiration channel, outer member, or both. The inner member may be rotated or oscillated by manipulating one or more of the user controls. The inner member may be rotated while stationary (i.e., not-reciprocating), or the inner member may be rotated while reciprocating.

The inner member may be reciprocated or axially moved along its center longitudinal axis, which may, or may not, be the same as the center or longitudinal axis of the aspiration channel, outer member, or both. The inner member may be reciprocated by manipulating one or more of the user controls. The inner member may be reciprocated while stationary (i.e., not-rotating), or the inner member may be reciprocated while rotating.

The medical device, the tubular assembly, the inner member, or a combination thereof may comprise one or more cutting portions. The cutting portion may function to shave, cut resect, abrade, or otherwise remove or separate tissue, bone, or the other anatomical features or objects from a surgical site.

The cutting portion may be located at a distal end or at a distal portion of the inner member. The cutting portion may be integrally formed with the inner member. The cutting portion may be mechanically attached to the inner member.

When the cutting portion is exposed or at least partially aligned with the outer member window, tissue, bone, or the other anatomical features or objects from a surgical site can be shaved, cut resected, abraded, or otherwise removed or separate. The cutting portion is exposed or at least partially aligned with the outer member window when the inner member is reciprocated or moved axially along a length of the outer member.

The inner member, the cutting portion, or both may comprise one or more inner member windows. At least a portion of the perimeter of the inner member window may include one or more teeth, blades, serrations, blades, sharp edges, or features that are adapted contact, engage, and then shave, cut, shear, resect, abrade, or otherwise remove or separate tissue, bone, or the other anatomical features or objects from a surgical site.

The inner member window is a window, gap, or opening defined in at least a portion of the length of the cutting portion or inner member.

The inner member window may be located anywhere along a length of the inner member. Preferably, however, the inner member window is aligned with or located proximal of any of the inner and/or outer member irrigation openings. However, in some configurations, it may be desirable to have the inner member window located distal of the inner and/or outer member irrigation openings. The outer member window may be generally aligned with the inner member window, or may be offset from the inner member window.

The inner member window may be a notch, groove, cutout, opening, or absence of material defined or existing in a portion of the circumference of an outer surface of the inner member. The inner member window may have edges at the perimeter of the outer member window defining the outer member window, which may be sharp or serrated to assist in shaving, cutting, resecting, abrading, or otherwise removing tissue, bone, or other anatomical features or objects at the surgical site.

The inner member window is in communication with the outer member cutting window and the aspiration channel defined within the inner member. Accordingly, during a medical procedure, pieces of the shaved, cut, resected, abraded, or removed tissue, bone, or the other anatomical features or objects and/or fluid from the surgical site can fall into and through the outer member window, into and through the inner member window, and then into the aspiration channel via gravity, and/or may be sucked or drawn into the aspiration channel via the cutting opening by way of the suction source.

The inner member may comprise one or more inner member irrigation openings. The inner member irrigation opening may function to provide a passageway, path, or opening into the inner member or aspiration channel so that irrigation fluid can be provided from the outer member irrigation opening, the irrigation supply channel, or both.

The inner member window may be a notch, groove, cutout, opening, or absence of material defined or existing in a portion of the circumference of an inner surface of the outer member. The inner member window may comprise a port, a socket, a fitting, or other structure for attaching to the inner member window.

The inner member may comprise any number or inner member irrigation openings. Preferably, the number or inner member irrigation openings corresponds to the number or outer member irrigation openings; however, in some configurations, it may be desirable to have more outer member irrigation openings than inner member irrigation openings. This may provide for distributing irrigation fluid into the aspiration channel at various locations, while receiving the irrigation fluid from the irrigation supply channel at one or more locations.

The inner member irrigation opening may be located anywhere on the inner member. For example, the inner member irrigation opening may be located at a distal-most end of the inner member. The inner member irrigation opening may be located proximal of the distal-most end of the inner member. The inner member irrigation opening may be generally aligned with the outer member irrigation opening, or may be offset from the outer member irrigation opening.

The inner member may comprise one or more aspiration channels. The aspiration channel may function to provide an area or passageway for the shaved, cut, resected, abraded, or removed tissue, bone, or the other anatomical features to be removed or pulled from the cutting portion of the inner member, from the windows of the inner and outer members, or a combination thereof. Air, irrigation fluid, anatomical fluids, or a combination thereof may also be removed from the surgical site by being moved proximally within the aspiration channel.

The aspiration channel may be in fluid communication with the suction source so that that fluids, shaved, cut, resected, abraded, or removed tissue, bone, or the other anatomical features, objects, and/or fluid removed from the surgical site can be drawn, pulled, aspirated, sucked, or otherwise removed from the surgical site, the cutting portion, the inner and outer windows, or a combination thereof.

The aspiration channel may be in fluid communication with the irrigation source so that that fluids, shaved, cut, resected, abraded, or removed tissue, bone, or the other anatomical features, objects, and/or fluid removed from the surgical site can be drawn, pulled, aspirated, sucked, or otherwise removed from the surgical site, the cutting portion, the inner and outer windows, or a combination thereof.

The aspiration channel may be a channel, bore, passageway, opening, hollow area, or a combination thereof defined in the inner member.

The aspiration channel may be in fluid communication with the inner and outer member irrigation openings so that irrigation fluid from the irrigation fluid supply channel and/or irrigation source can be provided or communicated into the aspiration channel.

The medical device may comprise one or more irrigation supply channels. The irrigation supply channel may function to provide a passageway or conduit for irrigation fluid from the irrigation supply to be provided or communicated to the medical device.

The irrigation supply channel may be a tube, a pipe, a conduit, a passageway, a hypotube, or a combination thereof that is in fluid communication with the irrigation source and the tubular assembly, the outer member irrigation window, the inner member irrigation window, the aspiration channel, or a combination thereof.

The irrigation supply channel may be located external to the medical device, the tubular assembly, the outer member, or a combination thereof. The irrigation supply channel may be attached directly to and/or in contact with an outside of the outer member. The irrigation supply channel may be separated from the outside of the outer member and only in contact with the outer member at the outer member irrigation opening where a distal port of the irrigation supply channel connects the supply channel and the tubular assembly, the outer member, the inner member, the aspiration channel, or a combination thereof. Because the irrigation supply channel is located outside of the tubular assembly, the outer member, or both, no irrigation fluid is provided inside the tubular assembly between the inner and outer members. More specifically, the medical device is free of any irrigation fluid flowing between the inner and outer members in a proximal or distal direction.

A gap may be defined between the inner and outer members. The gap may be a clearance between the inner and outer members so that the inner member can be moved and/or reciprocated within the outer member. The gap may be sufficiently small so that irrigation fluid does not drip, seep into, or pass into the gap while being communicated from the external irrigation supply channel into the aspiration channel. For example, the gap may be on the order of about 0.001" on each side. Additionally, or alternatively, the suction source may be sufficient to draw or pull the irrigation fluid into the aspiration channel from the irrigation channel, the outer member irrigation opening, the inner member irrigation opening, the inner member window, or a combination thereof without the irrigation fluid flowing or dripping or seeping into the gap. Additionally, or alternately, the irrigation source may comprise a pump to pressurize the irrigation fluid and force or pump the irrigation fluid into the aspiration channel so that the irrigation fluid does not have a chance to seep or drop or flow into the gap.

In some configurations, irrigation fluid may be provided to the medical device via this gap between the inner and outer members. That is, irrigation fluid may be pumped or provided from the irrigation source, into and through the gap in a distal direction, and then pumped or drawn into the aspiration channel, where the irrigation fluid is then brought back through the aspiration channel in a proximal direction. Providing the irrigation fluid into and through this gap in a distal direction is preferably in addition to providing the irrigation fluid into and through the external irrigation supply channel in a distal direction. However, it is understood that the medical device can be configured such that only the irrigation fluid is provided to the medical device through the gap and not through the external irrigation supply channel; only through the external irrigation supply channel and not through the gap; through both of the external irrigation supply channel and the gap; through the gap and then through the external supply channel; or a combination thereof.

Figure 1:
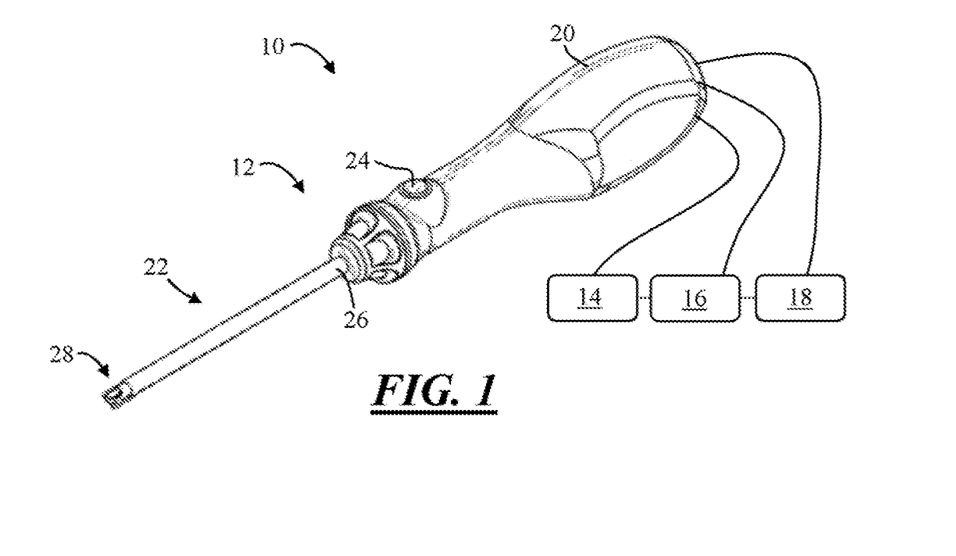
FIG. 1 is perspective view of a medical system comprising a medical device according to these teachings.

FIG. 1 illustrates a medical system 10. The medical system 10 comprises a medical device 12, an energy source 14, a suction source 16, and an irrigation source 18.

The medical device 12 comprises a hand piece 20 and a tubular assembly 22 extending from the hand piece 20. The hand piece 20 comprises one or more user controls 24 for operating the medical system 10, the medical device 12, the energy source 14, the suction source 16, the irrigation source 18, or a combination thereof.

The tubular assembly 22 comprises a proximal portion 26 located at the hand piece 20, and an opposing distal portion 28. While the distal portion 28 is illustrated as being a "straight shaft", where the distal portion 28 is generally straight and aligned with the rest of the tubular assembly 22, including the proximal portion 26, the distal portion 28 may bent or angled relative to the rest of the tubular assembly 22, including the proximal portion 26.

The energy source 14 is configured to power the medical system 10, the medical device 12, the suction source 16, the irrigation source 18, or a combination thereof.

The suction source 16, the irrigation source 18, or both are in fluid communication with the medical device 12, an aspiration channel 38 (FIG. 3) defined inside an inner member 32 (FIGS. 2, 3) of the tubular assembly 22, or both. The suction source 16 is configured to apply suction to, or pull vacuum from the medical device 12, the aspiration channel 38, or both. The irrigation source 18 is configured to supply an irrigation fluid to the medical device 12, the aspiration channel 38, or both.

Figure 2:
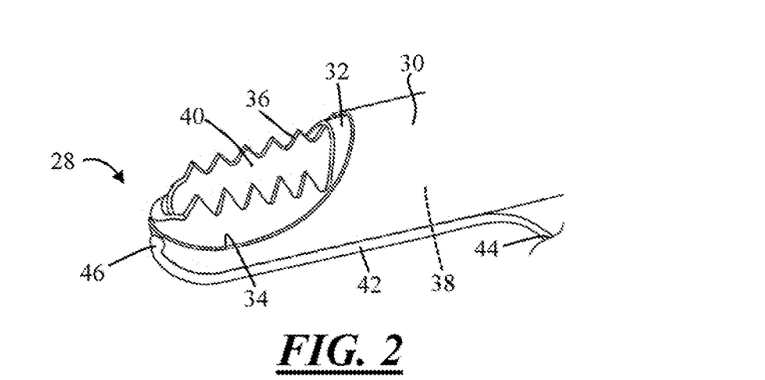
FIG. 2 is a perspective view of a distal portion of the medical device.

FIG. 2 illustrates an exemplary distal portion 28 of the tubular assembly 22 of the medical device 12. The tubular assembly 22 comprises a tubular outer member 30 and a tubular inner member 32 that is located inside of the outer tubular member 30. The outer member 30 comprises an outer member window 34, The inner member 32 comprises a cutting portion 36 and an aspiration channel 38 located inside of the inner member 32. The inner member 32 or the cutting portion 36 comprises an inner member window 40 that is in communication with the aspiration channel 38.

The medical device 12 comprises an irrigation supply channel 42. The irrigation supply channel 42 is located external to or outside of the outer member 30. The irrigation supply channel 42 at least partially extends along a length of the outer member 30. A proximal end of the irrigation supply channel 42 comprises a proximal irrigation port 44 that is in fluid communication with the irrigation source 18 (FIG. 1), and a distal end of the irrigation supply channel 42 comprises a distal irrigation port 46 that is attached to the medical device 12 or the outer member 30.

Figure 3:
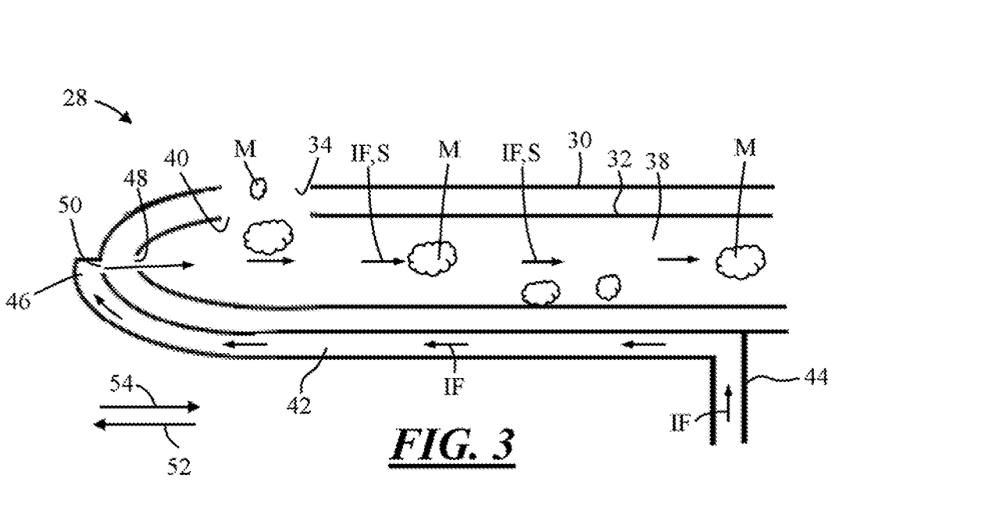
FIG. 3 is a cross-sectional view of a distal portion of the medical device.

FIG. 3 illustrates a cross-sectional view of an exemplary distal portion 28 of the tubular assembly 22 of the medical device 12. The inner member 32 is located inside of the outer member 30. The outer member 30 comprises an outer member irrigation opening 50. The inner member 32 comprises an inner member irrigation opening 48. These openings 50, 48 are generally aligned, and arranged at a distal-most end of the respective member 30, 32. However, one or both of these openings can be arranged at a location that is proximal of the distal-most end of a respective one of the members 30, 32.

The distal irrigation port 46 of the irrigation supply channel 42 is in fluid communication with the outer member irrigation opening 50. The outer member irrigation opening 50 is in fluid communication with the inner member irrigation opening 48 thus forming a fluid passageway between the two members 30, 32. The inner member irrigation opening 48 is in fluid communication with the aspiration channel 38. Therefore, irrigation fluid. IF can be supplied into the aspiration channel 38 from the irrigation supply channel 42 through the outer member irrigation opening 50, through the inner member irrigation opening 48, and into the aspiration channel 38. The suction source (FIG. 1) may then draw any matter M and/or irrigation fluid IF inside the aspiration channel 38 in a distal direction, as discussed further below.

The distal irrigation port 46 of irrigation supply channel 42, the outer member irrigation opening 50, and the inner member irrigation opening 48 are all located distal of the outer member window 34 and the inner member window 40.

Figure 4:
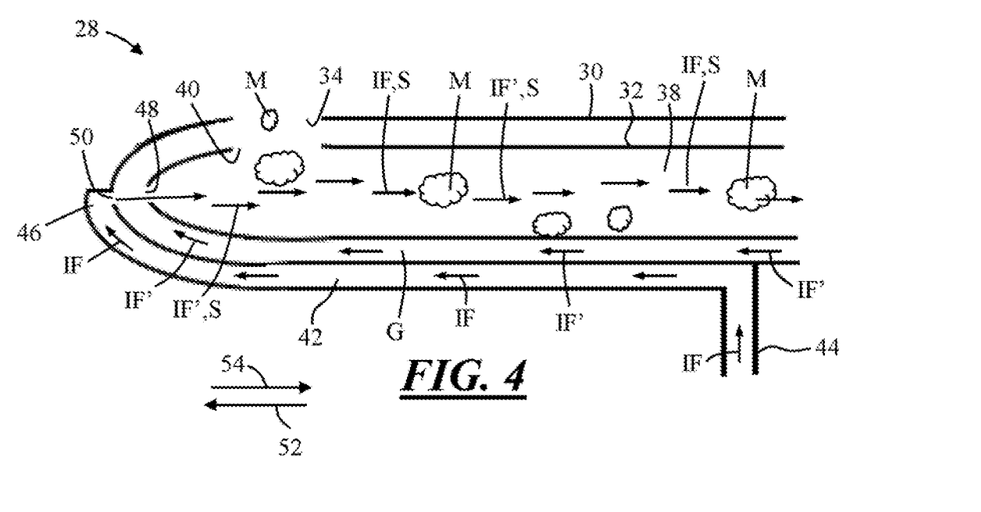
FIG. 4 is a cross-sectional view of a distal portion of the medical device.

FIG. 4 illustrates a cross-sectional view of an exemplary distal portion 28 of the tubular assembly 22 of the medical device 12, which may appear to be substantially similar to the FIG. 3, therefore only the differences will be described.

In addition to supplying irrigation fluid IF to the medical device via the irrigation supply channel 42, irrigation fluid IF' can also be supplied to the medical device by providing irrigation fluid IF' into a gap G defined between the inner and outer members 32, 30. The irrigation fluid IF' can flow through the gap G in a distal direction until the irrigation fluid IF' flows through the outer member irrigation opening 50, through the inner member irrigation opening 48, and into the aspiration channel 38. The suction source (FIG. 1) may then draw any matter M and/or irrigation fluid IF, IF' inside the aspiration channel 38 in a distal direction, as discussed further below.

Figure 5:
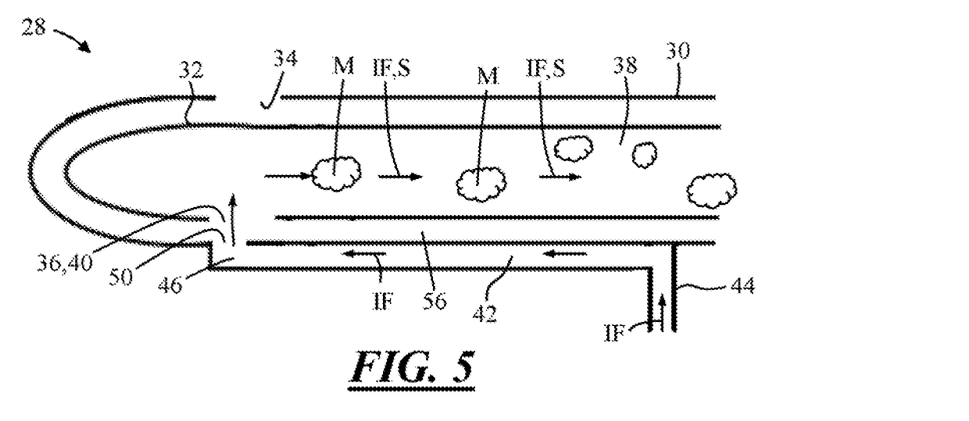
FIG. 5 is a cross-sectional view of a distal portion of the medical device.

FIG. 5 illustrates a cross-sectional view of an exemplary distal portion 28 of the tubular assembly 22 of the medical device 12, which includes at least some of the features illustrated and described at FIG. 3 and so only differences will be discussed.

The outer member 30 comprises an outer member irrigation opening 50, which is illustrated as being generally opposite the outer member window 34, but can be located anywhere adjacent the outer member window 34. The inner member 32 is free of any inner member irrigation openings.

The distal irrigation port 46 of the irrigation supply channel 42 is in fluid communication with the outer member irrigation opening 50. The inner member window 40 is in selective fluid communication with the outer member irrigation opening 50. Stated another way, the inner member 32 is configured to rotate and/or reciprocate within the outer member 30, and during the rotation and/or reciprocation of the inner member 32, the inner member window 40 becomes at least partially aligned with the outer member irrigation opening 50, and thus comes into fluid communication with the outer member irrigation opening 50. When the inner member window 40 is at least partially aligned with the outer member irrigation opening 50 and in fluid communication therewith, the cutting portion 36 of the inner member 32 is not aligned with and/or exposed through the outer member window 34, and thus tissue is not cut, shaved resected, and/or otherwise removed.

Regardless of the rotational and/or reciprocating position of the inner member 32, the inner member window 40 is in fluid communication with the aspiration channel 38. Therefore, when the inner member window 40 is aligned with and thus in fluid communication with the outer member irrigation opening 50, irrigation fluid IF can be supplied into the aspiration channel 38 from the irrigation supply channel 42, through the outer member irrigation opening 50, through the inner member window 40, and into the aspiration channel 38. The suction source (FIG. 1) may then draw any matter M and/or irrigation fluid IF inside the aspiration channel 38 in a distal direction, as discussed further below.

The irrigation fluid IF or IF' flows into the aspiration channel 38 when the inner member window 40 is aligned with or adjacent the outer member irrigation opening 50. Because the inner member 32 may oscillate at about 3,000 to about 5,000 rpm's, the inner member window 40 is in adjacent fluid communication with the outer member irrigation opening 50 several times per second.

When the inner member window 40 is not in fluid communication with the outer member irrigation opening 50, for example, when the inner member window 40 is at least partially aligned with and/or exposed through the outer member window 34, or at a rotational position therebetween, irrigation fluid IF can be supplied from the irrigation supply channel 42 to the outer member irrigation opening 50, but irrigation fluid IF cannot pass into or through the inner member window 40 and therefore cannot flow into the aspiration channel 38.

Figure 6:
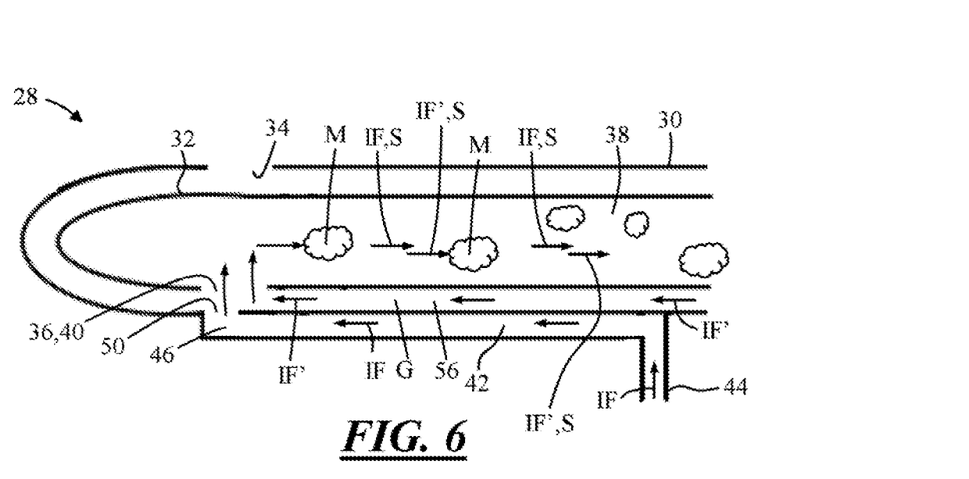
FIG. 6 is a cross-sectional view of a distal portion of the medical device.

FIG. 6 illustrates a cross-sectional view of an exemplary distal portion 28 of the tubular assembly 22 of the medical device 12, which may appear to be substantially similar to the FIG. 5, therefore only the differences will be described.

In addition to supplying irrigation fluid IF to the medical device via the irrigation supply channel 42, irrigation fluid IF' can also be supplied to the medical device by providing irrigation fluid IF' into a gap Ci defined between the inner and outer members 32, 30. The irrigation fluid IF' can flow through the gap G in a distal direction and then through the inner member window 40, and into the aspiration channel 38. The suction source (FIG. 1) may then draw any matter M and/or irrigation fluid. IF, IF' inside the aspiration channel 38 in a distal direction, as discussed further below.

The medical device 12 may comprise one or more magnets, encoders, or other suitable features or elements that may function to provide for the inner member 32 to align with the outer member 30 when the inner member 32 ceases to rotate and/or reciprocate. Preferably, in the configurations illustrated in FIGS. 5 and 6, the inner member 32 may align with the outer member 30 when the inner member 32 ceases to rotate and/or reciprocate such that the cutting portion 36 and inner member window 40 are aligned with the outer member irrigation opening 50. This may advantageously allow for irrigation fluid. IF and/or IF' to flow into the aspiration channel 38. This may function to advantageously remove any material M or clogs that may be present inside the aspiration channel 38 and/or cool the inner and/or outer members 32, 30.

A medical device may also be configured to include a combination of one or more elements and features of FIGS. 3-6.

Referring to FIGS. 1-6, the medical system 10 can be used in a medical procedure. The medical system 10, the medical device 12, or both can be used according to a method. The method steps disclosed herein can be performed in any order. Steps disclosed herein can be performed in any order, can be omitted, repeated, or a combination thereof.

The tubular assembly 22 of the medical device 12 can be inserted into a surgical site, such as a body cavity. Before or after the tubular portion 22 is inserted into a surgical site, the outer member 30 can be rotated to align the outer member window 34 with a site of interest. Before or after the tubular portion 22 is inserted into the surgical site and/or before or after the outer member 30 is rotated, the inner member 32 can be rotated and/or reciprocated relative to the outer member 30. When at least partially aligned with and exposed through the outer member window 34, the cutting portion 36 of the inner member 32 is configured to shave, cut, resect, abrade, or otherwise remove portions of an anatomical feature or object that it contacts.

By virtue of gravity and/or the suction source 16 acting on the aspiration channel 38, the cut, resected, abraded, or removed portions of the anatomical feature or object, hereafter matter M, is configured to fall into and/or is drawn through the outer member window 34 and the inner member window 40, and into the aspiration channel 38. At least some of the matter M may be drawn away from the windows 34, 40 in a proximal direction via the suction source 16, which is configured to pull vacuum or apply suction S in the aspiration channel 38 in a proximal direction 54.

Before, during, or after the cutting portion 36 of the inner member 32 shaves, cuts, resects, abrades, or otherwise removes portions of the anatomical feature or object, the irrigation source 18 is configured to supply irrigation fluid IF to the proximal irrigation port 44 of the irrigation supply channel 42. In some configurations (e.g., FIGS. 3 and 5) because the irrigation supply channel 42 is located outside of the outer member 30 and the tubular assembly 22, no irrigation fluid IF is passed between the inner and outer members 30, 32. Stated another way, the medical device 12 is free of any irrigation fluid IF flowing between the inner and outer members 30, 32 in a proximal or distal direction. Instead, the irrigation fluid IF is moved or configured to flow outside of the tubular assembly 22 and the outer member 30 via the irrigation supply channel 42 in a distal direction 52 from the proximal irrigation port 44 to the distal irrigation port 46.

In some other configurations, however, (e.g., FIGS. 4 and 6), irrigation fluid IF' is passed between the inner and outer members 30, 32 in a distal direction 52 to a distal portion of the medical device 12. This may be in addition to the irrigation fluid IF that flows outside of the tubular assembly 22 and the outer member 30 via the irrigation supply channel 42 in a distal direction 52.

Referring specifically to FIGS. 3 and 4, from the distal irrigation port 46, the irrigation fluid IF flows or is communicated through the outer member irrigation opening 50, the inner member irrigation opening 48, and ultimately into the aspiration channel 38. The irrigation fluid IF flows or is communicated through the outer member irrigation opening 50, the inner member irrigation opening 48, and ultimately into the aspiration channel 38 regardless of the rotational position of the inner member 32. That is, irrigation fluid IF can flow into the aspiration channel 38 regardless if the inner member window 40 or cutting portion 36 is or is not in rotational communication with or at least partially exposed through the outer member window 34. Advantageously, this may allow or provide for irrigation fluid IF to continuously flow into the aspiration channel 38 during a medical procedure regardless of the rotational position of the inner member 32. Once inside the aspiration channel 38, the irrigation fluid IF is moved in a proximal direction 54, and, in doing so, moves matter M located inside the aspiration channel 38 in a proximal direction and away from the windows 34, 40, which may advantageously to prevent or reduce chances of a buildup or clog of matter M inside the aspiration channel 38.

Referring specifically to FIGS. 5 and 6, when the inner member window 40 is at least partially aligned with the outer member irrigation opening 50, the irrigation fluid IF flows or is communicated from the distal irrigation port 46 to or through the outer member irrigation opening 50, to or through the inner member window 40, and ultimately into the aspiration channel 38.

The irrigation fluid IF flows or is communicated through the outer member irrigation opening 50, the inner member window 40, and ultimately into the aspiration channel 38 only when the rotational position of the inner member 32 is such that the inner member window 40 is at least partially aligned with the outer member irrigation opening 50. For example, when the cutting portion 36 of inner member 32 is at least partially aligned with or exposed through the outer member window 34, irrigation fluid IF is prevented from flowing into the aspiration channel 38 because the inner member window 40 is not at least partially aligned with the outer member irrigation opening 50.

LISTING OF REFERENCE NUMERALS

- 10 medical system
- 12 medical device
- 14 energy source
- 16 suction source
- 18 irrigation source
- 20 hand piece
- 22 tubular assembly
- 24 user controls
- 26 proximal portion of tubular assembly 22
- 28 distal portion of tubular assembly 22
- 30 outer member
- 32 inner member
- 34 outer member window
- 36 cutting portion of inner member 32
- 38 aspiration channel
- 40 inner member window
- 42 irrigation supply channel
- 44 proximal irrigation port of irrigation supply channel 42
- 46 distal irrigation port of irrigation supply channel 42
- 48 inner member irrigation opening
- 50 outer member irrigation opening
- 52 distal direction
- 54 proximal direction
- IF fluid flow
- M Matter
- S suction The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A debrider comprising:
   an outer member having a plurality of outer member irrigation openings;
   a first irrigation supply channel located outside of the outer member and configured to supply first irrigation fluid to the debrider, the irrigation supply channel comprising a distal irrigation port that is configured to fluidly connect the first irrigation supply channel to one outer member irrigation opening of the plurality of outer member irrigation openings;
   a second irrigation supply channel configured to supply second irrigation fluid to the debrider; and
   an inner member located inside of the outer member where the second irrigation supply channel is disposed between the first irrigation supply channel and the inner member, the inner member comprising a cutting portion and an aspiration channel, the cutting portion comprising an inner member window in communication with the aspiration channel, the inner member including a plurality of inner member irrigation openings separate from the inner member window and corresponding to the plurality of outer member irrigation openings, where one inner member irrigation opening of the plurality of inner member irrigation openings generally aligns with the one outer member irrigation opening, the one inner member irrigation opening being disposed at a distal tip of the inner member such that the one inner member irrigation opening remains aligned with the one outer member irrigation opening during operation of the debrider, the one inner member irrigation opening in fluid communication with both the aspiration channel and the one outer member irrigation opening of the outer member, the one inner member irrigation opening being configured to receive the first irrigation fluid from the first irrigation supply channel and the second irrigation fluid from the second irrigation supply channel, wherein the outer member comprises an outer member window through which the cutting portion of the inner member is exposed to shave tissue and the distal irrigation port, the one outer member irrigation opening, and the one inner member irrigation opening being located distal to the cutting portion of the inner member.

2. The debrider according to claim 1, wherein the distal irrigation port is located at a distal end of the outer member.

3. The debrider according to claim 1, wherein the irrigation fluid is communicated from the first irrigation supply channel through the outer member and the plurality inner member irrigation openings and into the aspiration channel.

4. The debrider according to claim 1, wherein the outer member irrigation opening is located at a distal most end of the outer member.

5. The debrider according to claim 1, wherein the one inner member irrigation opening and the one outer member irrigation opening are located distal of the outer member window.

6. A system comprising the debrider according to claim 1, wherein the system comprises a suction source that is in fluid communication with the aspiration channel and is configured to draw the irrigation fluid in a proximal direction through the aspiration channel.

7. A method comprising:
inserting the debrider according to claim 1 into a surgical site, and
cutting tissue with the cutting portion of the inner member at the surgical site.

8. A debrider comprising:
an outer member comprising a plurality of outer irrigation openings where one outer member irrigation opening of the plurality of outer member irrigation openings is located at a distal-most end thereof;
a first irrigation supply channel configured to supply first irrigation fluid in a distal direction, through the outer member irrigation opening and into an aspiration channel, the aspiration channel configured to flow irrigation fluid in a proximal direction, wherein the irrigation supply channel is located outside of the outer member;
a second irrigation supply channel configured to supply second irrigation fluid to the debrider; and
an inner member located inside of the outer member and proximal the outer member irrigation opening where the second irrigation supply channel is disposed between the first irrigation supply channel and the inner member, the inner member comprising the aspiration channel and a plurality of inner member irrigation openings that correspond to the plurality of outer member irrigation openings, where one inner member irrigation opening of the plurality of inner member irrigation openings is disposed at a distal tip of the inner member and aligns with the one outer member irrigation opening such that the one inner member irrigation opening remains aligned with the one outer member irrigation opening during operation of the debrider, the one inner member irrigation opening being configured to receive the first irrigation fluid from the first irrigation supply channel and the second irrigation fluid from the second irrigation supply channel.

9. The debrider according to claim 8, wherein the one inner member irrigation opening is in fluid communication with both of the aspiration channel and the one outer member irrigation opening and through which the irrigation fluid is configured to pass.

10. The debrider according to claim 9, wherein the inner member comprises a cutting portion, and wherein the one outer member irrigation opening and the one inner member irrigation opening are located distal the cutting portion of the inner member.

* * * * *